United States Patent [19]

Suzuki

[11] Patent Number: Plant 7,739

[45] Date of Patent: Dec. 10, 1991

[54] ROSE PLANT—KEITAIBU VARIETY

[75] Inventor: Seizo Suzuki, Tokyo, Japan

[73] Assignee: The Conard-Pyle Company, West Grove, Pa.

[21] Appl. No.: 552,501

[22] Filed: Jul. 16, 1990

[30] Foreign Application Priority Data

Oct. 20, 1989 [FR] France ..... 8882

[51] Int. Cl.[5] ..... A01H 5/00

[52] U.S. Cl. ..... Plt./18

[58] Field of Search ..... Plt./18, 19

*Primary Examiner*—James R. Feyrer

*Attorney, Agent, or Firm*—Burns, Doane, Swecker & Mathis

[57] ABSTRACT

A new and distinct variety of Hybrid Tea rose plant is provided which abundantly forms attractive double pink blossoms. The blossoms are rose bengal on the upper surface and rhodamine pink on the under surface, and may vary to the darker tones according to the stage of the growing season. Such blossoms are long lasting when cut and placed in a vase. The plant exhibits an upright growth habit, vigorous vegetation, and is well suited for cut flower production when grown in a greenhouse. The foliage has an attractive bright dark green appearance which serves to well complement the blossom coloration. Additionally, the plant exhibits very good disease resistance.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the product of the pollination of the Sweet Promise variety (U.S. Plant Pat. No. 3,095) with an unnamed seedling (nonpatented in the United States). The Sweet Promise variety commonly is known as the Sonia variety in the United States. The male parent (i.e., the pollen parent) was an unnamed seedling (nonpatented in the United States). The parentage of the new variety can be summarized as follows:

[Sweet Promise × Unnamed Seedling] × Unnamed Seedling.

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance attractive long lasting double blossoms which are bengal rose on the upper surface and rhodamine pink on the lower surface,
(b) exhibits an upright growth habit,
(c) forms very attractive dark green foliage which serves to complement the blossom coloration,
exhibits vigorous vegetation,
(e) is particularly suited for cut flower production, and
(f) exhibits very good disease resistance.

The bud and blossom coloration may vary to the darker tones depending upon the stage of the growing season.

The new variety well meets the needs of the horticultural industry for a number of uses and is particularly well suited for cut flower production.

The new variety has been found to undergo asexual propagation by a number of routes, including budding, grafting, cuttage. etc. The characteristics of the new variety have been found to be strictly transmissable by such asexual propagation fron one generation to another.

The new variety has been named the Keitaibu variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during November while budded on *Rosa indicia* understock and growing in greenhouses at Cap d'Antibes, France.

DETAILED DESCRIPTION

Figures 1, 2, 3, 4, 5, 6, 7, 8, 9, 10, 11, 12, 13, 14, 15, 16:
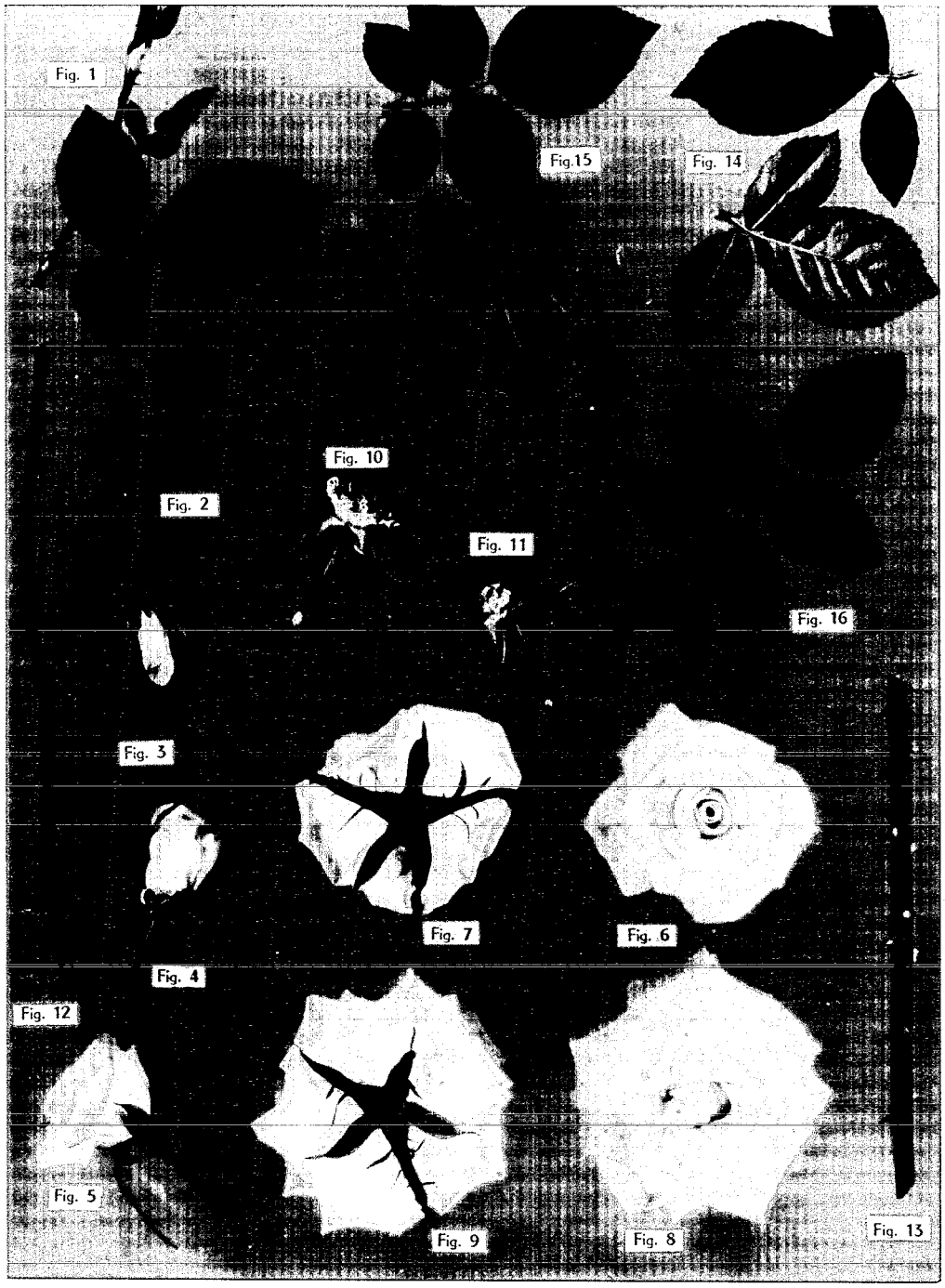
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of an open flower—plan view—obverse.
FIG. 7 illustrates a specimen of an open flower—plan view—reverse.
FIG. 8 illustrates a specimen of a fully open flower immediately prior to petal drop—plan view—obverse.
FIG. 9 illustrates a specimen of a fully open flower immediately prior to petal drop—plan view—reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch shown upside down.
FIG. 14 illustrates specimens of two leaves with three leaflets—plan view—upper surface (top) and under surface (bottom)
FIG. 15 illustrates specimens of two leaves with five leaflets—plan view—upper surface (top) and under surface (bottom)
FIG. 16 illustrates a specimen of a leaf with seven leaflets—plan view—upper surface.

The chart used in the identification of the colors is that of The Royal Horticultural Society (R.H.S. Colour Chart). The description is based on the observation of two year old plants made during November while budded on *Rosa indicia* understock and growing in greenhouses at Cap d'Antibes, France. The coloration in common terms precedes reference to the chart.

Class: Hybrid Tea.

Plant:

*Height.*—Plants which were pruned to a height of 85 cm. produce floral stems having a length of approximately 40 to 60 cm. When grown in the field at Wasco, Calif., one year old plants from which one blossom cutting has been taken, commonly will assume a height of approximately 1 to 1.3 m. at the end of the growing season.

*Habits.*—Upright.

Branches:

*Color.*—Young stems: bright bronze green, Yellow-Green Group 146A. Adult wood: bronze green, Yellow-Green Group 146A.

*Thorns.*—Size: average. Quantity: sometimes numerous. Color: pinkish on young stems and pinkish green on adult wood.

Leaves:

*Stipules.*—Adnate, pectinate, wide and linear.

*Petioles.*—Upper surface: striped reddish brown on young foliage and medium green on adult foliage with more or less glandular edges. Under surface: light green, bear very few prickles.

*Leaflets.*—Number: 3, 5, and 7. Shape: oval. Serration: single and regular. Texture: consistent. General Appearance: foliage is fairly dense, bright and very attractive. Color (young foliage): Upper surface: bronze green, Yellow-Green Group 146A. Under Surface: medium green, Green Group 138B, more or less stained with reddish brown coloration. Color (adult foliage): Upper Surface: dark green, Green Group 137A. Under Surface: dark medium green, Green Group 138B.

Inflorescence:

*Number of flowers.*—Usually one per stem.

*Peduncle.*—Medium green in coloration and bears numerous pediculate glands. The length is approximately 12 cm. on average.

*Sepals.*—Upper surface: tomentose, greenish in coloration. Under surface: light green in coloration, the outer sepals commonly have small appendiculate edges and have a small leaflike appendix at the tip.

*Buds.*—Shape: conical. Length: approximately 3 cm. on average. Size: medium. Color upon opening: Upper surface: rose bengal, Red-Purple Group 61D, widely suffused with medium rose bengal, Red-Purple Group 61C. Under surface: rhodamine pink, Red-Purple Group 62A, slightly suffused with medium rose bengal, Red-Purple Group 61C. The bud coloration can vary into darker tones depending upon the season.

*Flower.*—Shape: elongated and double. Diameter: approximately 9 cm. on average. Color (when opening begins): Upper surface: rose bengal, Red-Purple Group 61D, widely suffused with medium rose bengal, Red-Purple Group 61C. Under surface: rhodamine pink, Red-Purple Group 62A. Color (when blooming): Upper surface: rose bengal, Red-Purple Group 61D, widely suffused with medium rose bengal, Red-Purple Group 61C, lighter on the outside petals. Under surface: rhodamine pink, Red-Purpose Group 62A, slightly suffused with medium rose bengal, Red-Purple Group 61C, lighter on the outside petals. Color (at end of opening): Upper surface: rose bengal, Red-Purple Group 61D, suffused with medium rose bengal, Red-Purple Group 61C, lighter on the outside petals. Under surface: rhodamine pink, Red-Purple Group 62A, lighter on the outside petals. The flower coloration can vary into the darker tones depending upon the season. Fragrance: none. Lasting quality: long. Petal number: approximately 31 on average, including a few which may not be completely formed. Texture: consistent. Petal drop: very good. Stamen number: approximately 115 on average. Anthers: ochre with insertion at the end. Filaments: light fuschia in coloration, of irregular heights. Pistils: approximately 127 on average. Stigmas: normal, strawlike. Styles: dark fuschia, very tomentose at the base, fairly twisted, of irregular heights. Receptacle: smooth, medium green, in longitudinal section it is in the shape of a wide funnel.

Development:

*Vegetation.*—Vigorous.

*Blooming.*—Abundant.

*Resistance to diseases.*—Very good.

*Aptitude to forcing.*—Average.

I claim:

1. A new and distinct variety of Hybrid Tea rose plant characterized by the following combination of characteristics:

(a) forms in abundance attractive long lasting double blossoms which are bengal rose on the upper surface and rhodamine pink on the lower surface,
(b) exhibits an upright growth habit,
(c) forms very attractive dark green foliage which serves to complement the blossom coloration,
(d) exhibits vigorous vegetation,
(e) is particularly suited for cut flower production, and
(f) exhibits very good disease resistance:

substantially as herein shown and described.

* * * * *